(12) United States Patent
Salloum (10) Patent No.: US 8,875,882 B1
(45) Date of Patent: Nov. 4, 2014

(54) HOLDER AND DISPOSAL DEVICE FOR HYPODERMIC NEEDLES

(71) Applicant: Maan G. Salloum, University Place, WA (US)

(72) Inventor: Maan G. Salloum, University Place, WA (US)

( * ) Notice: Subject to any disclaimer, the term of this patent is extended or adjusted under 35 U.S.C. 154(b) by 0 days.

(21) Appl. No.: 13/863,496

(22) Filed: Apr. 16, 2013

(51) Int. Cl.
*B65D 83/02* (2006.01)
*A61J 1/00* (2006.01)

(52) U.S. Cl.
CPC ........................................ *A61J 1/00* (2013.01)
USPC .......................................................... 206/366

(58) Field of Classification Search
USPC ............ D24/131; 83/944; 206/353–367, 370, 206/63.5
See application file for complete search history.

(56) References Cited

U.S. PATENT DOCUMENTS

| | | | |
|---|---|---|---|
| 4,255,996 A * | 3/1981 | Choksi et al. ................... | 83/140 |
| D274,159 S | 6/1984 | Simicich | |
| 4,494,652 A * | 1/1985 | Nelson et al. .................. | 206/366 |
| 4,738,362 A * | 4/1988 | Burns et al. .................... | 206/366 |
| 4,802,645 A | 2/1989 | Chiodo | |
| D325,438 S * | 4/1992 | Salekfard et al. ............ | D24/131 |
| 5,201,720 A | 4/1993 | Borgia et al. | |
| 5,356,384 A * | 10/1994 | Haber ........................... | 604/110 |
| 5,797,885 A | 8/1998 | Rubin | |
| D482,448 S | 11/2003 | Crawford | |
| 6,848,157 B2 | 2/2005 | Abe | |
| 6,976,349 B2 | 12/2005 | Baldwin et al. | |

\* cited by examiner

*Primary Examiner* — Mickey Yu
*Assistant Examiner* — Allan Stevens (57) ABSTRACT

A holder and disposal device for hypodermic needles safely detaches a needle from a syringe, permits use of multiple needles in sequence, and allows for the re-capping of needles without accidental puncture. The device includes a container having an interior space configured for receiving needles and needle covers. A top edge of the container defines an opening into the interior space. A lid is couplable to the container and is positionable in a closed position to cover the opening and in an open position to expose the opening. A gap is positioned in the lid. A clamp is couplable to the lid proximate the gap wherein pivoting the clamp opens and closes a pair of jaws above the gap such that the needles and needle covers positioned over the needles extend through the gap when the jaws are clamped onto the needle cover.

15 Claims, 6 Drawing Sheets

HOLDER AND DISPOSAL DEVICE FOR HYPODERMIC NEEDLES

BACKGROUND OF THE DISCLOSURE

Field of the Disclosure

The disclosure relates to holder and disposal devices and more particularly pertains to a new holder and disposal device for safely and efficiently detaching a needle from a syringe, permitting use of multiple needles in sequence, and allowing for the re-capping of needles without accidental puncture to the medical provider.

SUMMARY OF THE DISCLOSURE

An embodiment of the disclosure meets the needs presented above by generally comprising a container having an interior space configured for receiving needles and needle covers. A top edge of the container defines an opening into the interior space. A lid is couplable to the container and is positionable in a closed position to cover the opening and in an open position to expose the opening. A gap is positioned in the lid. A clamp is couplable to the lid proximate the gap wherein pivoting the clamp opens and closes a pair of jaws above the gap such that the needles and needle covers positioned over the needles extend through the gap when the jaws are clamped onto the needle cover There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
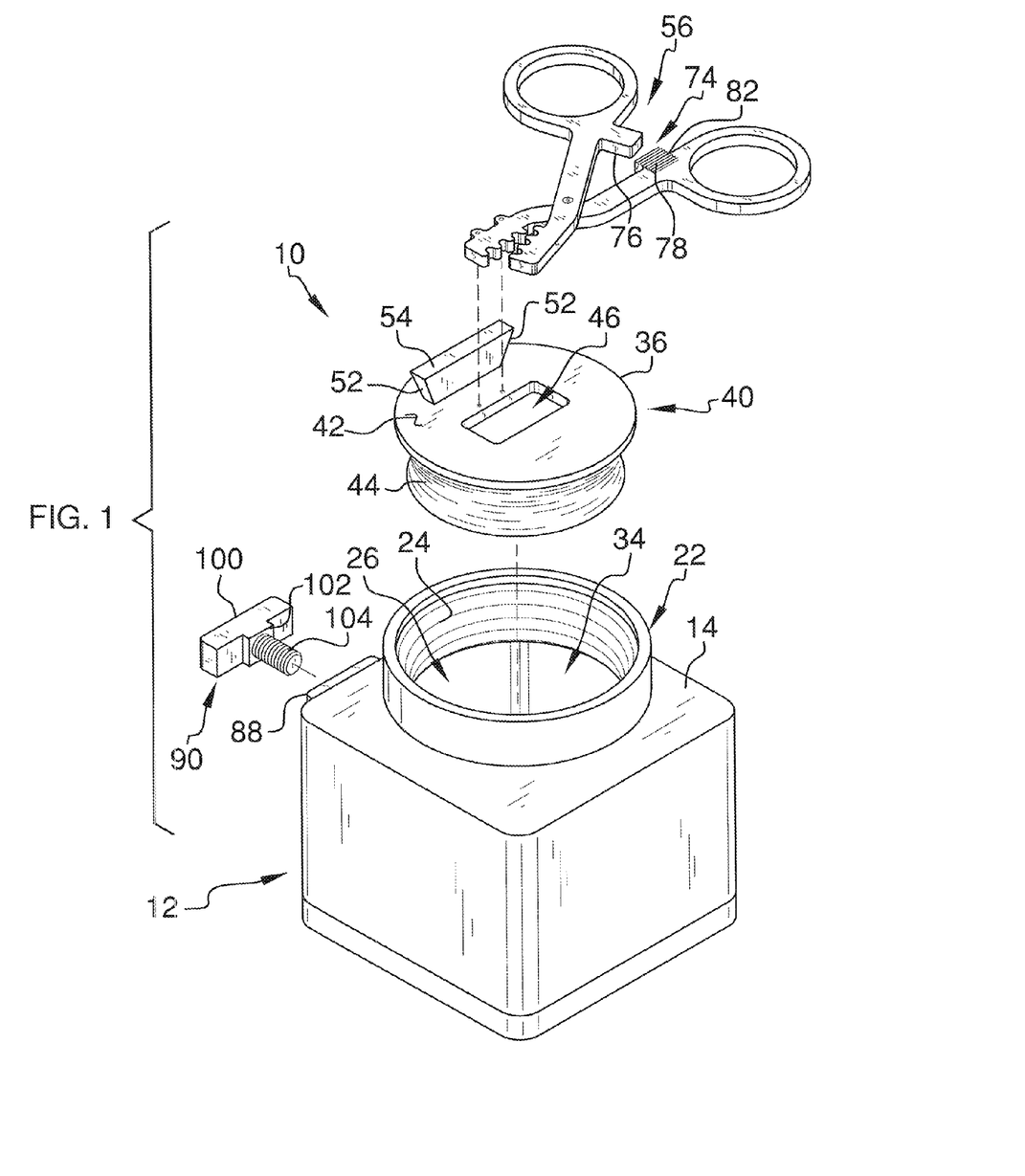
FIG. 1 is a top front side perspective view of a holder and disposal device for hypodermic needles according to an embodiment of the disclosure.
Figure 2:
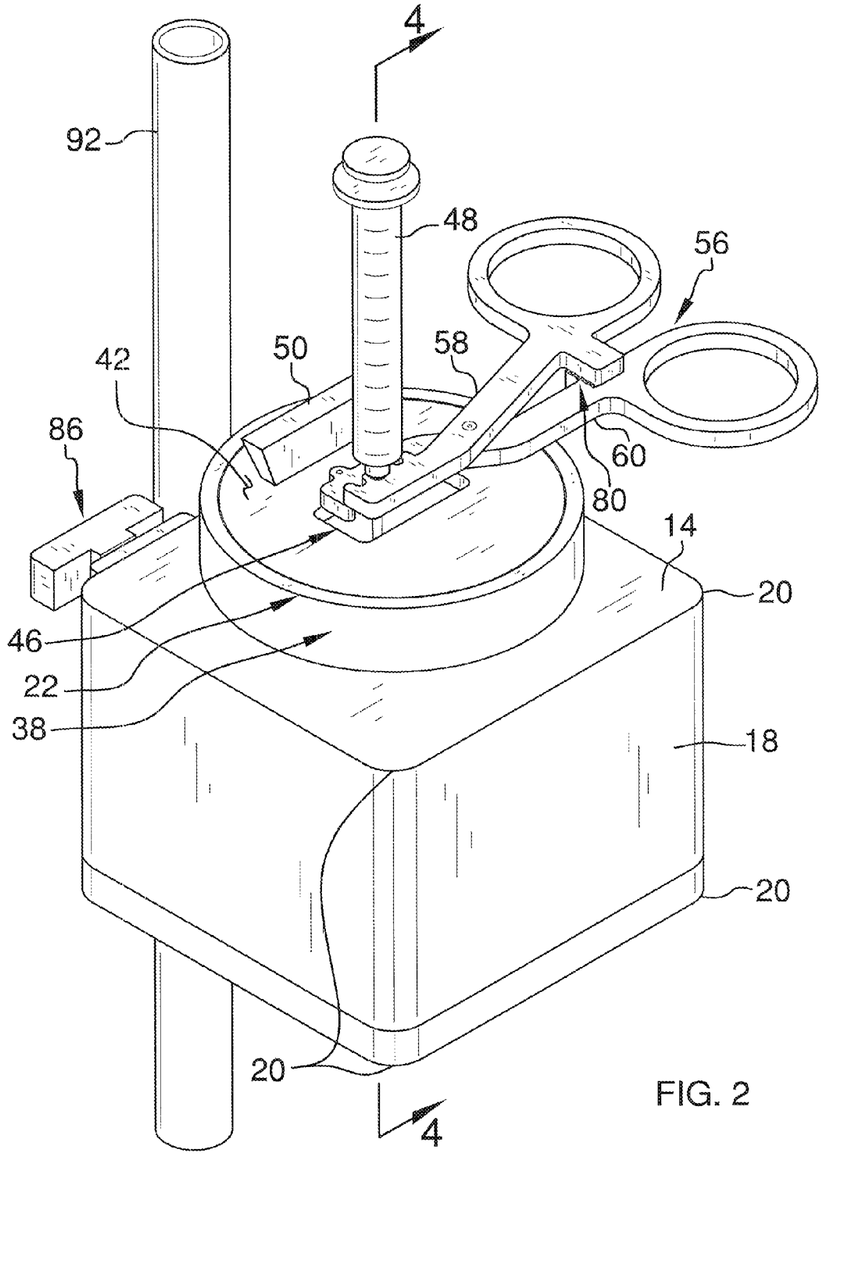
FIG. 2 is a top front side perspective view of an embodiment of the disclosure.
Figure 3:
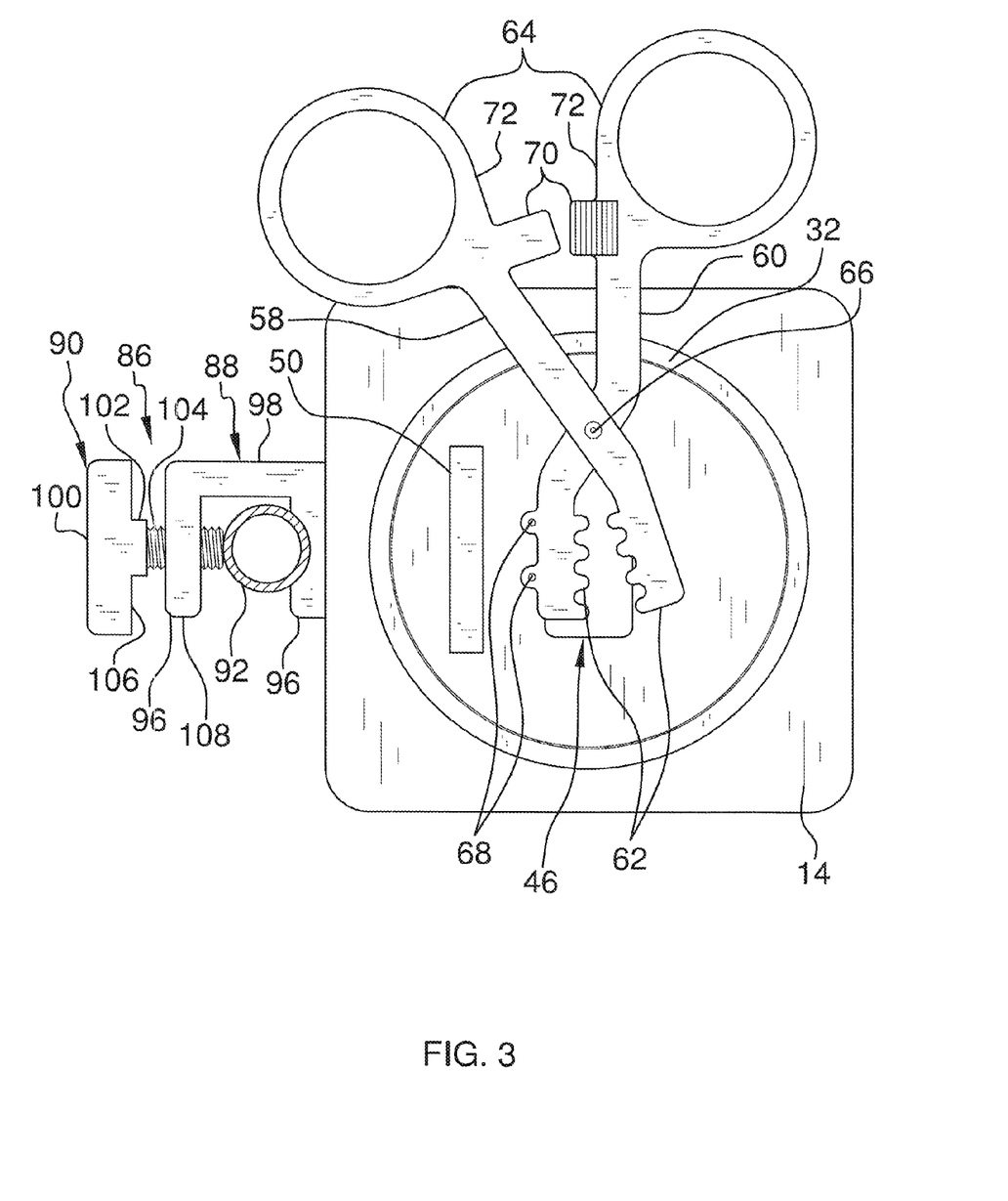
FIG. 3 is a top view of an embodiment of the disclosure.
Figure 4:
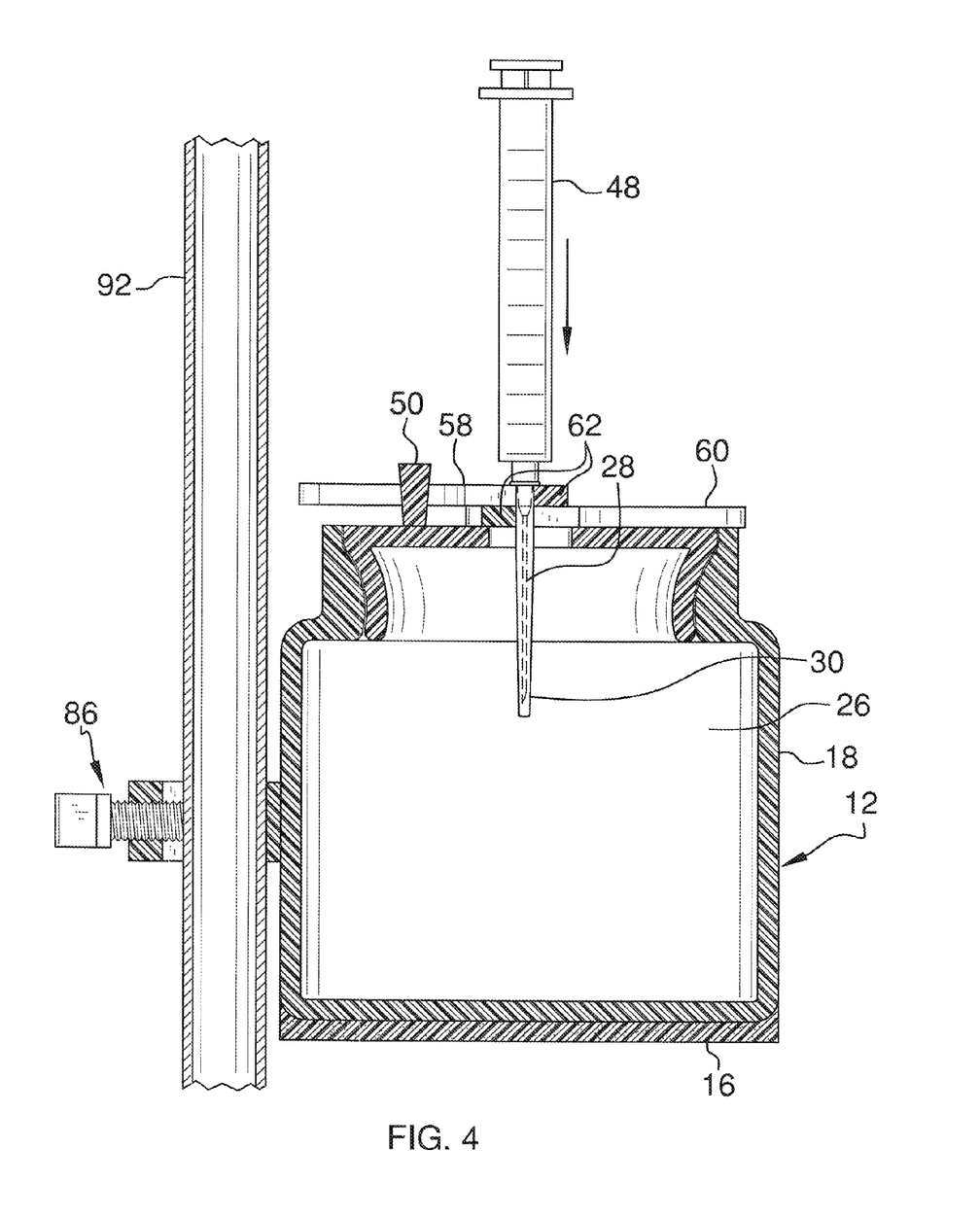
FIG. 4 is a cross-sectional view of an embodiment of the disclosure taken along line 4-4 of FIG. 2.
Figure 5:
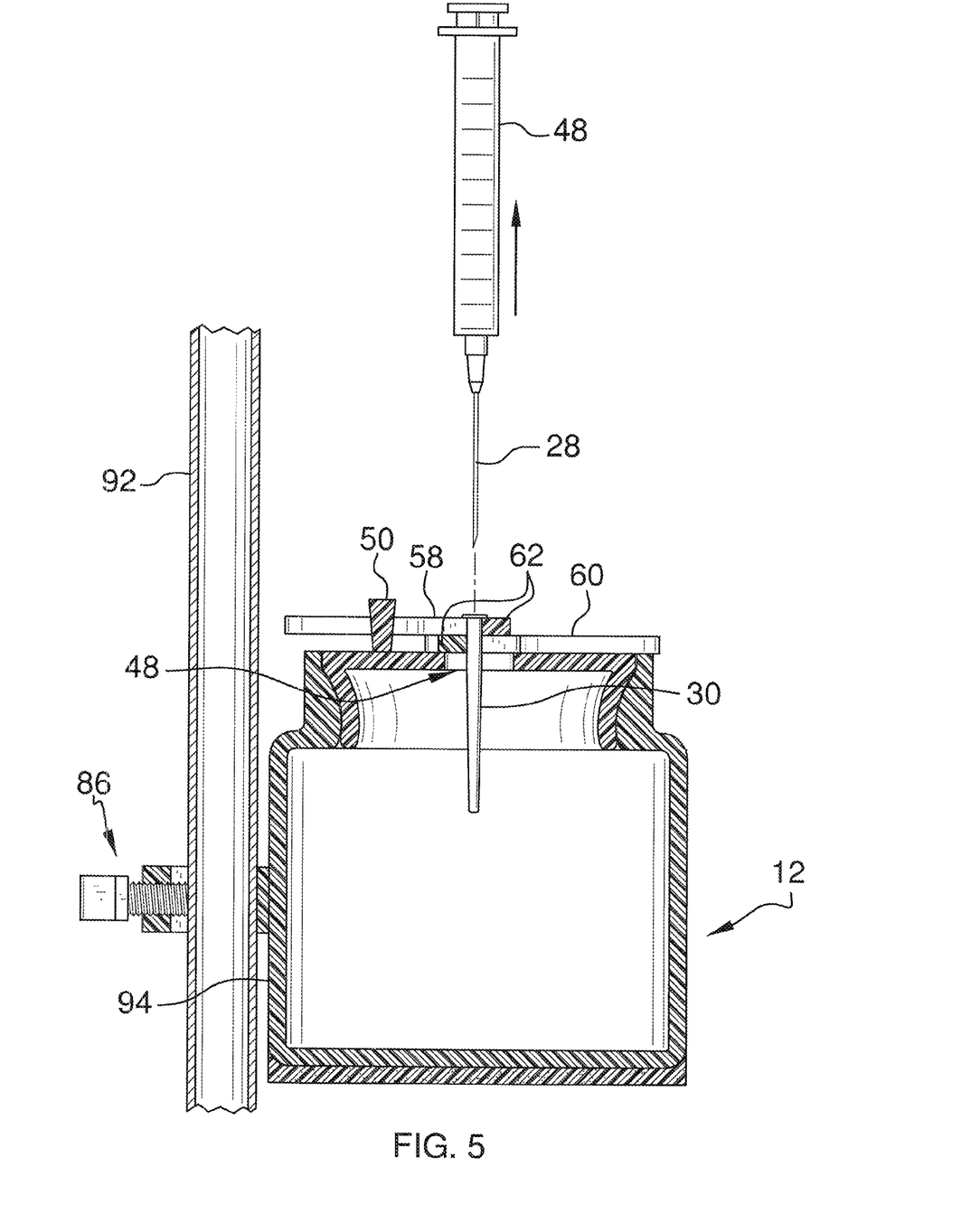
FIG. 5 is a cross-sectional view of an embodiment of the disclosure similar to FIG. 4, except that FIG. 5 shows the needle cover retained in the clamp while the syringe and needle are detached from the needle cover.
Figure 6:
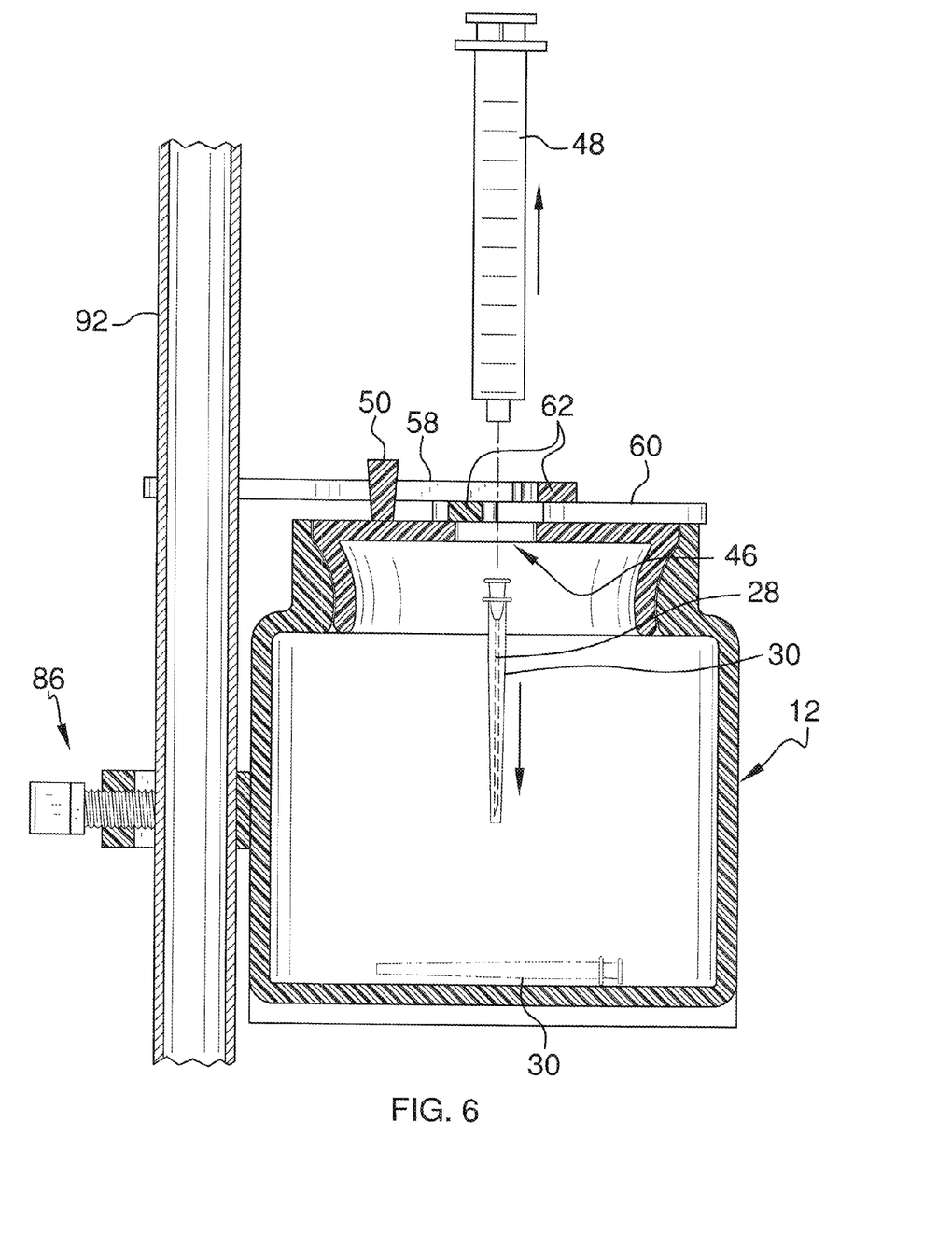
FIG. 6 is a cross-sectional view of an embodiment of the disclosure similar to FIGS. 4 and 5, except that FIG. 6 shows the needle and needle cover detached from the syringe while the needle cover and needle positioned therein are falling downwardly into the container.

With reference now to the drawings, and in particular to FIGS. 1 through 6 thereof, a new holder and disposal device embodying the principles and concepts of an embodiment of the disclosure and generally designated by the reference numeral 10 will be described.

As best illustrated in FIGS. 1 through 6, the holder and disposal device for hypodermic needles 10 generally comprises a container 12 having a top wall 14 opposite a bottom wall 16 and a peripheral wall 18 extending upwardly from the bottom wall 16. The container 12 may have a plurality of rounded edges 20. The container 12 may have an outwardly projecting lip 22 extending upwardly from the top wall 14. The lip 22 is preferably annular and offset from the peripheral wall 18. An inner side 24 of the lip 22 may be threaded. An interior space 26 of the container 12 is defined by the top wall 14, the bottom wall 16, and the peripheral wall 18 wherein the interior space 26 is configured for receiving hypodermic needles 28 and needle covers 30 therein.

A top edge 32 of the container 12 defines an opening 34 into the interior space 26. The lip 22 preferably extends a full length around the opening 34. A lid 36 is couplable to the container 12 wherein the lid 36 is positionable in a closed position 38 to cover the opening 34 and in an open position 40 to expose the opening 34. The lid 36 comprises a top surface 42 and a lower portion 44 wherein the lower portion 44 extends downwardly from the top surface 42. The lower portion 44 is abuttable against the inner side 24 of the lip 22 when the lid 36 is coupled to the container 12. The lower portion 44 may be concavely arcuate. The lid 36 may be annular and disposed of separately from the container 12. A gap 46 is positioned in the lid 36. The gap 46 may be centrally positioned in the top surface 42 of the lid 36. The gap 46 has a size and shape configured to prevent a syringe 48 attached to the needle 28 from extending therethrough. The gap 46 is preferably rectangular. A grip 50 may be coupled to the lid 36. The grip 50 preferably extends outwardly from the top surface 42 of the lid 36 wherein the grip 50 is configured for manual grasping by a user to facilitate transfer of the lid 36. The grip 50 has a pair of side portions 52 and a top portion 54. The top portion 54 extends between each of the side portions 52. The side portions 52 may be angled outwardly away from one another.

A clamp 56 has a first member 58 and a second member 60. The first member 58 may be positioned above the second member 60. Each of the first 58 and second 60 members has an associated jaw 62 positioned distally relative to a handle 64. The jaws 62 are preferably serrated. The first member 58 is moveable relative to the second member 60, and the second member 60 is preferably stationary. The jaws 62 are coupled to a pivot point 66 such that urging of the handles 64 together slides the first member 58 toward the second member 60 such that the jaws 62 are configured for retaining the needle cover 30 therebetween when the jaws 62 are slid together. The clamp 56 may be couplable to the lid 36 via a quick-release attachment 68. The clamp 56 is positioned parallel to the gap 46. The second member 60 is couplable to the lid 36 proximate the gap 46 wherein pivoting of the first member 58 opens and closes the jaws 62 above the gap 46 such that the needle 28 and needle cover 30 positioned over the needle 28 extend through the gap 46 when the jaws 62 are clamped onto the needle cover 30. The clamp 56 is disposed of after caring for one patient.

A pair of projections 70 may be coupled to the clamp 56. Each of the projections 70 is coupled to an associated one of the first 58 and second 60 members. Each of the projections 70 extends outwardly from an inner side 72 of an associated one of the handles 64 such that closing the jaws 62 of the clamp 56 causes the projections 70 to overlap. A clasp 74 is coupled to the clamp 56. The clasp 74 has a first portion 76 and a second portion 78 each coupled to an associated one of the projections 70. The first portion 76 of the clasp 74 is coupled to a bottom side 80 of the projection 70 of the first member 58 and the second portion 78 of the clasp 74 is coupled to a top side 82 of the projection 70 of the second member 60 wherein closing the jaws 62 of the clamp 56 causes the first 76 and second 78 portions of the clasp 74 to overlap such that the clasp 74 retains the jaws 62 in a closed position 84. The clasp 74 may provide for adjustable locking of the clamp 56. The clasp 74 may use a serrated slide, snaps, or the like to secure the projections, and the corresponding jaws 62, in place.

A fastener 86 is couplable to the container 12. The fastener 86 comprises a first clamping member 88 and a second clamping member 90. The first 88 and second 90 clamping members may couple the container 12 to a vertical support structure 92 such that the first 88 and second 90 clamping members are configured for positioning the vertical support structure 92 between the first 88 and second 90 clamping members. The vertical support structure 92 may include an intravenous pole, a wall, or the like. When the support structure 92 is a wall, an inverted groove-wedged triangle is coupled to the container 12 in order to secure the container 12 to the wall. The device 10 may also be freestanding and positioned on a counter, table, cart, or the like. A key may be used to lock the fastener 86 to the container 12. The first clamping member 88 may be positioned on a first side 94 of the peripheral wall 18. The first clamping member 88 comprises a pair of side portions 96 and a medial portion 98 extending between each of the side portions 96. The second clamping member 90 comprises a main portion 100, a projection 102, and a screw 104 wherein the projection 102 extends outwardly from an inside face 106 of the main portion 100 and the screw 104 extends outwardly from the projection 102. The screw 104 extends into a first one 108 of the side portions 96 of the first clamping member 88 and is configured to abut the vertical support structure 92 when the first clamping member 88 is coupled to the second clamping member 90.

An opening 34 of the container 12 has a diameter between 2.0 cm and 8.0 cm. Similarly, the top surface 42 of the lid 36 has a diameter between approximately 2.0 cm and 8.0 cm so as to correspond to the size of the opening 34. The lip 22 has a thickness between approximately 2 mm and 10 mm. The height of the lid 36 is between approximately 1.0 cm and 5.0 cm. The gap 46 has a length between approximately 1.0 cm and 4.0 cm and a width between approximately 0.25 cm and 3.0 cm. The handles 64 have a diameter between approximately 1.0 cm and 5.0 cm. The distance from the pivot point 66 to the end of the jaws 62 measures between approximately 1.0 and 6.0 cm.

Similarly, the distance from the pivot point 66 to the clasp 74 measures between approximately 1.0 cm and 6.0 cm. The grip 50 has a length between approximately 1.0 cm and 6.0 cm and width between approximately 0.5 cm and 5.0 cm.

In use, as stated above and shown in the Figures, the needle cover 30 and a covered needle 28 is placed between the jaws 62 of the clamp 56. The clasp 74 secures the jaws around the needle cover 30 and enables the jaws 62 to securely retain the needle cover 30 therebetween. In this manner, the needle 28 is able to be re-capped by inserting the needle 28 back into the needle cover 30 and releasing the clasp 74 on the clamp 56. The needle cover 30 is disposed into the container 12 by clamping tighter onto the needle cover 30 when the needle cover 30 is held between the jaws 62 and then opening the jaws 62 to permit the needle cover 30 to fall into the interior space 26. To also dispose of the needle 28, the same is done while the needle 28 is positioned within the needle cover 30.

The container 12 can be freestanding and mounted on a table, countertop, or the like or secured to a vertical support structure 92 using the fastener 86. The grip 50 is used to facilitate transfer of the lid 36.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A holder and disposal device configured for engaging hypodermic needles comprising:

a container having a top wall opposite a bottom wall and a peripheral wall extending upwardly from said bottom wall, said container including an outwardly projecting lip extending upwardly from said top wall, said lip being offset from said peripheral wall, an inner side of said lip being threaded;

an interior space of said container being defined by said bottom wall, said top wall, and said peripheral wall wherein said interior space is configured for receiving at least one hypodermic needle and needle cover therein;

a top edge of said container defining an opening into said interior space, said lip extending a full length around said opening;

a lid couplable to said container wherein said lid is positionable in a closed position to cover said opening and in an open position to expose said opening, said lid comprising a top surface and a lower portion wherein said lower portion extends downwardly from said top surface, said lower portion being concavely arcuate, said lower portion being abuttable against said inner side of said lip when said lid is coupled to said container;

a gap positioned in said top surface of said lid, said gap having a size and shape configured to prevent a syringe of the hypodermic needle from extending therethrough; and a clamp having a pair of jaws, said clamp being couplable to said lid proximate said gap wherein pivoting said clamp opens and closes said jaws above said gap such that the needle and needle cover positioned over the needle are configured to extend through said gap when said jaws are clamped onto the needle cover.

2. A holder and disposal device configured for engaging hypodermic needles comprising:

a container having a top wall opposite a bottom wall and a peripheral wall extending upwardly from said bottom wall;

an interior space of said container being defined by said bottom wall, said top wall, and said peripheral wall wherein said interior space is configured for receiving at least one hypodermic needle and needle cover therein;

a top edge of said container defining an opening into said interior space;

a lid couplable to said container wherein said lid is positionable in a closed position to cover said opening and in an open position to expose said opening;

a gap positioned in a top surface of said lid, said gap having a size and shape configured to prevent a syringe of the hypodermic needle from extending therethrough; and a clamp having a pair of jaws, said clamp being couplable to said lid proximate said gap wherein pivoting said clamp opens and closes said jaws above said gap such that the needle and needle cover positioned over the needle are configured to extend through said gap when said jaws are clamped onto the needle cover, said clamp having a first member and a second member, said first member being positioned above said second member, each of said first and second members having an associated one of said jaws positioned distally relative to an associated handle, said jaws being coupled to a pivot point such that urging of said handles together slides said jaws together.

3. The device of claim 2, further comprising said first member being moveable relative to said second member, said second member being stationary, said second member being couplable to said lid proximate said gap.

4. The device of claim 1, further comprising said jaws being serrated.

5. The device of claim 1, further comprising said clamp being couplable to said lid via a quick-release attachment.

6. The device of claim 1, further comprising said clamp being positioned parallel to said gap.

7. The device of claim 2, further comprising:
a pair of projections coupled to said clamp, each of said projections being coupled to an associated one of said first and second members, each of said projections extending outwardly from an inner side of an associated one of said handles such that closing said jaws of said clamp causes said projections to overlap; and a clasp coupled to said clamp, said clasp having a first portion and a second portion each coupled to an associated one of said projections, said first portion of said clasp being coupled to a bottom side of said projection of said first member and said second portion of said clasp being coupled to a top side of said projection of said second member wherein closing said jaws of said clamp causes said first and second portions of said clasp to overlap such that said clasp retains said jaws in a closed position.

8. The device of claim 1, further comprising a fastener couplable to said container, said fastener comprising a first clamping member and a second clamping member, said first and second clamping members being configured for coupling said container to a vertical support structure such that said first and second clamping members position the vertical support structure between said first and second clamping members.

9. The device of claim 8, further comprising said first clamping member being positioned on a first side of said peripheral wall, said first clamping member comprising a pair of side portions and a medial portion extending between each of said side portions, said second clamping member comprising a main portion, a projection, and a screw wherein said projection extends outwardly from an inside face of said main portion and said screw extends outwardly from said projection, said screw extending into a first one of said side portions of said first clamping member and being configured to abut the vertical support structure when said first clamping member is coupled to said second clamping member.

10. The device of claim 1, further comprising:
said container having a plurality of rounded edges, said lip being annular;

said lid being annular;

said gap being centrally positioned in said top surface of said lid said gap being rectangular;

a clamp having a first member and a second member, said first member being moveable relative to said second member, said second member being stationary, said first member being positioned above said second member, each of said first and second members having an associated one of said jaws positioned distally relative to a handle, said jaws being serrated, said jaws being coupled to a pivot point such that urging of said handles together slides said first member toward said second member such that said jaws are configured for retaining the needle cover therebetween when said jaws are slid together, said clamp being couplable to said lid via a quick-release attachment, said clamp being positioned parallel to said gap, said second member being couplable to said lid proximate said gap wherein pivoting of said first member opens and closes said jaws above said gap such that the needle and needle cover positioned over the needle are configured to extend through said gap when said jaws are clamped onto the needle cover;

a pair of projections coupled to said clamp, each of said projections being coupled to an associated one of said first and second members, each of said projections extending outwardly from an inner side of an associated one of said handles such that closing said jaws of said clamp causes said projections to overlap;

a clasp coupled to said clamp, said clasp having a first portion and a second portion each coupled to an associated one of said projections, said first portion of said clasp being coupled to a bottom side of said projection of said first member and said second portion of said clasp being coupled to a top side of said projection of said second member wherein closing said jaws of said clamp causes said first and second portions of said clasp to overlap such that said clasp retains said jaws in a closed position;

a fastener couplable to said container, said fastener comprising a first clamping member and a second clamping member, said first and second clamping members being configured for coupling said container to a vertical support structure such that said first and second clamping members position the vertical support structure between said first and second clamping members, said first clamping member being positioned on a first side of said peripheral wall, said first clamping member comprising a pair of side portions and a medial portion extending between each of said side portions, said second clamping member comprising a main portion, a projection, and a screw wherein said projection extends outwardly from an inside face of said main portion and said screw extends outwardly from said projection, said screw extending into a first one of said side portions of said first clamping member and being configured to abut the vertical support structure when said first clamping member is coupled to said second clamping member; and a grip coupled to said lid, said grip extending outwardly from said top surface of said lid wherein said grip is configured for manual grasping by a user to facilitate transfer of said lid, said grip having a pair of side portions and a top portion, said top portion extending between each of said side portions, said side portions being angled outwardly away from one another.

11. The device of claim 2, further comprising said jaws being serrated.

12. The device of claim 2, further comprising said clamp being couplable to said lid via a quick-release attachment.

13. The device of claim 2, further comprising a fastener couplable to said container, said fastener comprising a first clamping member and a second clamping member, said first and second clamping members being configured for coupling said container to a vertical support structure such that said first and second clamping members position the vertical support structure between said first and second clamping members.

14. The device of claim 13, further comprising said first clamping member being positioned on a first side of said peripheral wall, said first clamping member comprising a pair of side portions and a medial portion extending between each of said side portions, said second clamping member comprising a main portion, a projection, and a screw wherein said projection extends outwardly from an inside face of said main portion and said screw extends outwardly from said projection, said screw extending into a first one of said side portions of said first clamping member and being configured to abut the vertical support structure when said first clamping member is coupled to said second clamping member.

15. The device of claim 2, further comprising said clamp being positioned parallel to said gap.

* * * * *